United States Patent
Palero et al.

(10) Patent No.: US 12,144,585 B2
(45) Date of Patent: Nov. 19, 2024

(54) ILLUMINATION COMPENSATION IN IMAGING

(71) Applicant: KONINKLIJKE PHILIPS N.V., Eindhoven (NL)

(72) Inventors: Jonathan Alambra Palero, Waalre (NL); Steffie Petronella Akkermans, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 127 days.

(21) Appl. No.: 17/781,753

(22) PCT Filed: Dec. 21, 2020

(86) PCT No.: PCT/EP2020/087356
§ 371 (c)(1),
(2) Date: Jun. 2, 2022

(87) PCT Pub. No.: WO2021/123404
PCT Pub. Date: Jun. 24, 2021

(65) Prior Publication Data
US 2023/0026168 A1    Jan. 26, 2023

(30) Foreign Application Priority Data
Dec. 20, 2019   (EP) .................................... 19218928

(51) Int. Cl.
*A61B 5/00* (2006.01)
*A61B 5/1171* (2016.01)
(Continued)

(52) U.S. Cl.
CPC .......... *A61B 5/0077* (2013.01); *A61B 5/1176* (2013.01); *G06V 10/141* (2022.01);
(Continued)

(58) Field of Classification Search
CPC ...... H04N 23/71; H04N 23/74; G06V 10/141; G06V 10/60; G06V 20/64; G06V 40/10;
(Continued)

(56) References Cited

U.S. PATENT DOCUMENTS

| 9,414,780 | B2 | 8/2016 | Rhoads |
| 9,922,452 | B2* | 3/2018 | Son ........................ G06T 15/80 |
| 10,482,346 | B2* | 11/2019 | Kim ....................... G06V 10/50 |
| 11,116,407 | B2* | 9/2021 | Dickie ................... H04N 5/265 |

(Continued)

FOREIGN PATENT DOCUMENTS

| EP | 1229835 B1 | 8/2002 |
| EP | 2050385 B1 | 4/2011 |
| KR | 20180082172 A | 7/2018 |

OTHER PUBLICATIONS

Three-dimensional maps of human skin properties on full face with shadows using 3D-hyperspectral imaging Gevaux et al. 16 pages (Year: 2019).*
International Search Report and Written Opinion Dated Apr. 14, 2021 for International Application No. PCT/EP2020/087356 Filed Dec. 21, 2020.
(Continued)

*Primary Examiner* — Twyler L Haskins
*Assistant Examiner* — John H Morehead, III

(57) ABSTRACT

In an embodiment, a method (100) is described. The method comprises obtaining (102) a three-dimensional representation of a body surface. The method further comprises obtaining illumination information for the three-dimensional representation that is indicative of an orientation of the body surface relative to a reference axis. The method further comprises determining illumination compensation information (104). The illumination compensation information is used (106) to compensate for an illumination variation apparent from the illumination information in an image of the body surface.

20 Claims, 4 Drawing Sheets

(51) Int. Cl.
- *G06V 10/141* (2022.01)
- *G06V 10/60* (2022.01)
- *G06V 20/64* (2022.01)
- *G06V 40/10* (2022.01)
- *G06V 40/16* (2022.01)
- *H04N 23/71* (2023.01)
- *H04N 23/74* (2023.01)

(52) U.S. Cl.
CPC .............. *G06V 10/60* (2022.01); *G06V 20/64* (2022.01); *G06V 40/10* (2022.01); *G06V 40/161* (2022.01); *H04N 23/71* (2023.01); *H04N 23/74* (2023.01)

(58) Field of Classification Search
CPC ................ G06V 40/161; A61B 5/0077; A61B 5/1176; A61B 2576/02; A61B 5/441; G06T 17/00; G06T 2207/30201
See application file for complete search history.

(56) References Cited

U.S. PATENT DOCUMENTS

| | | | |
|---|---|---|---|
| 2011/0182520 A1* | 7/2011 | Free | G06V 40/164 345/426 |
| 2015/0109417 A1 | 4/2015 | Zirnheld | |
| 2019/0150724 A1 | 5/2019 | Elazar | |
| 2019/0336003 A1* | 11/2019 | Patwardhan | G06T 7/174 |

OTHER PUBLICATIONS

Written Opinion of the International Preliminary Examining Authority Dated Jul. 7, 2021 for International Application No. PCT/EP2020/087356 Filed Dec. 21, 2020.

International Preliminary Report on Patentability Dated Apr. 22, 2022 for International Application No. PCT/EP2020/087356 Filed Dec. 21, 2020.

Zhao, et al: "Minimizing Illumination Differences for 3D to 2D Face Recognition Using Lighting Maps", IEEE Transactions on Cybernetics, vol. 44, No. 5, May 2014.

* cited by examiner

ILLUMINATION COMPENSATION IN IMAGING

CROSS REFERENCE TO RELATED APPLICATIONS

This application is the U.S. National Phase application under 35 U.S.C. § 371 of International Application No. PCT/EP2020/087356 filed Dec. 21, 2020, which claims the benefit of European Patent Application Number 19218928.0 filed Dec. 20, 2019. These applications are hereby incorporated by reference herein.

FIELD OF THE INVENTION

The invention relates to a method, apparatus and tangible machine-readable medium for use in imaging, for example, in certain illumination settings.

BACKGROUND OF THE INVENTION

A topic of interest in the field of non-obtrusive measurement and monitoring relates to skin sensing for personal care and health applications. Skin sensing systems are being developed that promise skin quantification and monitoring of features in skin that may offer users information that is too small to detect, too faint to notice or too slow to follow. To deliver results that are acceptable to users, such skin sensing systems may need to provide sensitivity and specificity when performing skin sensing. Providing measurements taken by such skin sensing systems are proven to be robust and reliable, users may establish trust in these skin sensing systems.

It is known, e.g. from US patent application US 2011/182520 A1 to derive the location of a light source illuminating a subject from an image of that object. Based on this, the orientation of the subject might be determined.

Imaging-based skin sensing systems may need to determine information that could be affected by difficult-to-control parameters such as ambient illumination. For example, certain uncontrolled environments such as at a user's home may feature undefined and/or potentially varying ambient illumination. Such uncontrolled environments may lead to erroneous measurements of a user's skin, which may in turn lead to unacceptable or untrusted results for the user. Consequently, any personal care or health treatment regime based on such results may be compromised.

The performance of other imaging-based sensing systems for acquiring information from a surface other than skin may also be adversely affected by certain uncontrolled environments. For example, a user wishing to acquire an image of an object for a certain application in an uncontrolled environment may find that the image may feature unacceptable illumination variation, which may affect how the image is perceived or subsequently processed.

Accordingly, an object is to improve imaging in certain illumination settings.

SUMMARY OF THE INVENTION

Aspects or embodiments described herein relate to improving imaging in certain illumination settings. Aspects or embodiments described herein may obviate one or more problems associated with imaging in an uncontrolled environment.

In a first aspect, a method is described. The method is a computer-implemented method. The method comprises obtaining a three-dimensional representation of a body surface. The method further comprises obtaining illumination information for the three-dimensional representation. The illumination information is indicative of an orientation of the body surface relative to a reference axis. The method further comprises determining illumination compensation information configured to normalize an illumination variation apparent from the illumination information. The method further comprises determining the orientation of the body surface based on an analysis of a three-dimensional reconstruction of the body surface. The method further comprises using the illumination compensation information to compensate for the illumination variation in an image of the body surface. The method further comprises determining, from the image compensated for the illumination variation, information for characterizing skin of the body surface.

The three-dimensional reconstruction may be derived from imaging data for the body surface.

In some embodiments, the information for characterizing skin comprises a measurement of the skin for determining a course of action as part of a personal care application.

In some embodiments, determining the illumination compensation information comprises determining a normalization map representing a plurality of spatial locations of the body surface. Each spatial location may be associated with an illumination compensation factor to apply to a corresponding spatial location of the image to correct for the illumination variation in the image.

In some embodiments, the illumination information comprises a three-dimensional illumination map representing a plurality of spatial locations of the body surface. Each spatial location of the illumination map may be associated with an illumination parameter indicative of at least one of: a property of an illumination source; and a relative position of the illumination source with respect to the spatial location.

In some embodiments, the method comprises determining the illumination information by obtaining imaging data for the body surface. The method may further comprise estimating the illumination parameter for the spatial location of the body surface based on an analysis of the obtained imaging data. The analysis may take into account the orientation of the body surface.

In some embodiments, the property of the illumination source comprises at least one of: a luminance of the illumination source; and a divergence of the illumination source.

In some embodiments, determining the illumination compensation information comprises obtaining imaging data for the body surface. The method may further comprise determining the illumination information based on the obtained imaging data. The method may further comprise identifying any illumination variations apparent from the illumination information to determine the illumination compensation information.

In some embodiments, determining the illumination information from the imaging data comprises comparing the imaging data with previously-obtained imaging data to determine whether or not the imaging data has been obtained in a previous time frame. If the imaging data has not been obtained previously, the method may comprise generating the illumination information from the imaging data. The method may further comprise causing the illumination information associated with the imaging data to be stored in a memory. If the imaging data has been obtained previously, the method may comprise obtaining the illumination information associated with the imaging data from the memory.

In some embodiments, obtaining the three-dimensional representation of the body surface comprises obtaining imaging data for the body surface. The method may further comprise determining the three-dimensional representation based on the obtained imaging data.

In some embodiments, determining the three-dimensional representation from the imaging data comprises determining whether or not the body surface can be recognized by checking a memory storing a database of any previously identified body surfaces. If the body surface is not recognized, the method may comprise determining the three-dimensional representation from the imaging data. The method may further comprise causing the three-dimensional representation associated with the body surface to be stored in a memory. If the body surface is recognized, the method may comprise obtaining the three-dimensional representation associated with the recognized body surface from the memory.

In some embodiments, the body surface comprises a face of a subject. The three-dimensional representation may comprise a three-dimensional reconstruction of the face.

In some embodiments, using the illumination compensation information to compensate for the illumination variation in the image of the body surface comprises obtaining the image of the body surface. The method may further comprise compensating for the illumination variation in the image using the illumination compensation information.

In a second aspect, apparatus is described. The apparatus comprises processing circuitry. The processing circuitry comprises an obtaining module. The obtaining module is configured to obtain a three-dimensional representation of a body surface. The obtaining module is further configured to obtain illumination information for the three-dimensional representation. The illumination information is indicative of an orientation of the body surface relative to a reference axis. The processing circuitry further comprises a determining module. The determining module is configured to determine illumination compensation information configured to normalize an illumination variation apparent from the illumination information. The determining module is further configured to determine the orientation of the body surface based on an analysis of a three-dimensional reconstruction of the body surface derived from imaging data for the body surface. The processing circuitry further comprises a correcting module. The correcting module is configured to use the illumination compensation information to compensate for the illumination variation in an image of the body surface. The determining module is further configured to determine, from the image compensated for the illumination variation, information for characterizing skin of the body surface.

In some embodiments, the apparatus further comprises an imaging module. The imaging module may be configured to cause an imaging device to acquire the image of the body surface.

In a third aspect, a tangible machine-readable medium is described. The tangible machine-readable medium stores instructions which, when executed by at least one processor, cause the at least one processor to obtain a three-dimensional representation of a body surface. The instructions further cause the at least one processor to obtain illumination information for the three-dimensional representation. The illumination information is indicative of an orientation of the body surface relative to a reference axis. The instructions further cause the at least one processor to determine illumination compensation information configured to normalize an illumination variation apparent from the illumination information. The instructions further cause the at least one processor to determine the orientation of the body surface based on an analysis of a three-dimensional reconstruction of the body surface derived from imaging data for the body surface. The instructions further cause the at least one processor to use the illumination compensation information to compensate for the illumination variation in an image of the body surface. The instructions further cause the at least one processor to determine, from the image compensated for the illumination variation, information for characterizing skin of the body surface.

These and other aspects of the invention will be apparent from and elucidated with reference to the embodiment(s) described hereinafter.

BRIEF DESCRIPTION OF THE DRAWINGS

Exemplary embodiments of the invention will now be described, by way of embodiment only, with reference to the following drawings, in which.

DETAILED DESCRIPTION OF THE EMBODIMENTS

Figure 1:
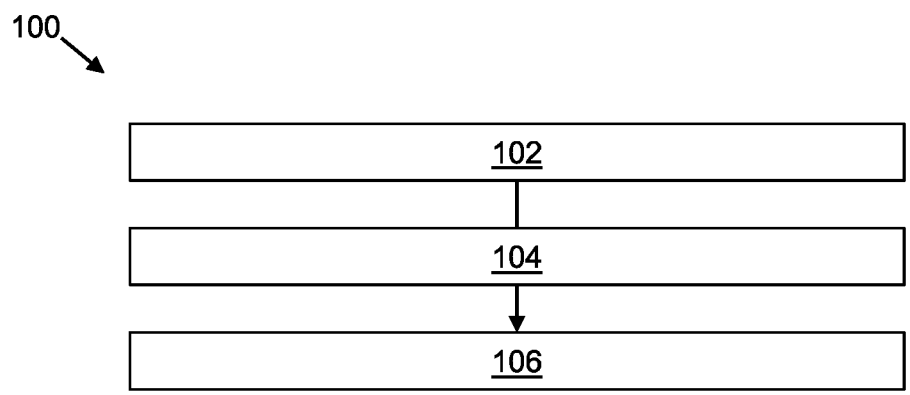
FIG. 1 refers to a method of improving imaging in certain illumination settings according to an embodiment.

FIG. 1 shows a method 100 (e.g., a computer-implemented method) of improving imaging in certain illumination settings. For example, imaging may be affected by certain illumination settings such as in uncontrolled environments where the illumination is undefined and/or potentially varying. As will be described in more detail below, the method 100 may correct for any undefined and/or potentially varying illumination in uncontrolled environments such as in a subject's home.

The method 100 comprises, at block 102, obtaining a three-dimensional representation of a body surface.

The three-dimensional representation of the body surface may refer to a three-dimensional map or surface profile of the body surface. For example, a three-dimensional representation may be generated for a surface of a body such as part of a human body (e.g., a face, torso or limb) or any other body (e.g., including an inanimate body such as a product or other object). The three-dimensional representation may comprise a map of vertices (e.g., position coordinates) corresponding to positions on the surface of the body. In some examples, the three-dimensional representation may be representative of a polygon mesh, which may be defined in terms of at least one of: a set of vertices, edges connecting adjacent vertices and faces defined by a closed set of edges (e.g., a triangle, quad face or other polygonal shape).

The three-dimensional representation may comprise a dataset that refers to certain features of the body surface. For example, certain dataset elements may comprise an indication of the vertices defining the surface of the body and/or any information which can be used to define the three-dimensional representation. Thus, the three-dimensional representation may refer to any information which can be used to illustrate or generate a three-dimensional replica of the surface of the body.

Block 102 of the method 100 further comprises obtaining illumination information for the three-dimensional representation. The illumination information may be indicative of an orientation of the body surface relative to a reference axis.

Illumination information for the three-dimensional representation may refer to a distribution of the illumination on the body surface. This distribution of illumination may be indicative of the orientation of the body surface relative to the reference axis. In some examples, the body surface may be in a certain illumination setting where the distribution of illumination on the body surface may provide information regarding a relationship between a source of illumination and the body surface. For example, if the apparent intensity of illumination at a certain part of the body surface is greater than the apparent intensity of illumination at another part of the body surface, this may indicate that the certain part of the body surface is facing and/or is closer to the source of illumination the other part of the body surface. In other words, by analyzing the distribution of illumination on the body surface, it may be possible to determine or estimate the orientation of the body surface relative to the reference axis.

The reference axis may refer to an axis about which the body surface may rotate and thereby define the orientation of the body surface. More than one reference axis may be defined such that rotation about the at least one axis may vary the orientation of the body surface. The reference axis may be defined in relation to the three-dimensional representation. For example, the three-dimensional representation for the body surface may be determined and the reference axis or axes may be defined in relation to the three-dimensional representation.

The method 100 further comprises, at block 104, determining illumination compensation information to compensate for an illumination variation apparent from the illumination information.

The illumination variation apparent from the illumination information for the three-dimensional representation may be indicative that the illumination for the body surface is undefined and/or potentially varying (e.g., spatially varying and/or varying as a function of time). For example, the body surface may have an uneven illumination distribution as a result of the undefined and/or potentially varying illumination. The illumination compensation information may provide the compensation for a distribution of illumination determined from imaging data acquired for a particular illumination setting.

The illumination compensation information may comprise an illumination compensation factor associated with a spatial location on the body surface. Each spatial location on the body surface may be associated with a certain illumination parameter such as intensity and/or spectral content (e.g., red, green and blue intensity levels), which can be determined from imaging data for the body surface. In some cases, an evenly distributed illumination may yield the same illumination parameter value at each spatial location. However, an unevenly distributed illumination may yield different illumination parameter values for different spatial locations on the body surface.

The illumination compensation factor may be determined according to the particular distribution of illumination determined for the body surface in a particular illumination setting. Thus, the illumination compensation factor for a particular spatial location could be applied to the determined illumination parameter value at that spatial location so that any illumination variation can be compensated.

In some examples, the illumination compensation information may normalize the illumination variation across the body surface. For example, if a particular spatial location on the body surface is determined to be illuminated with an intensity that is 10% higher than another spatial location, the illumination compensator factor for one or both of the particular spatial location and the other spatial location could be calculated to compensate for the illumination variation. In this case, the illumination compensation factor for the particular spatial location could indicate that the detected intensity at the particular location is to be reduced by a factor of 1.1 (e.g., to compensate for the 10% higher intensity at that particular location)—although other ways to normalize the illumination variation may be used.

The method 100 further comprises, at block 106, using the illumination compensation information to compensate for the illumination variation in an image of the body surface.

Once the illumination compensation information has been determined for a certain illumination setting, an illumination variation in the image of the body surface may be compensated for such that the illumination distribution across the body surface meets certain criteria. Such criteria may comprise, for example, evenness of illumination distribution such that each location on the body surface appears to be illuminated evenly.

The criteria may define a range of illumination parameter values (e.g., intensity level, spectral content, and so on) considered acceptable for the application concerned. For example, a particular application may determine illumination parameter values from the image and that application may make a decision based on the illumination parameter values while assuming that there any no illumination variations.

That is, the application may incorrectly assume that the illumination setting is appropriate for its intended purpose. If the illumination parameter values for the image are not within an acceptable range, any resulting decision making may be compromised since this decision making may not take into account any illumination variation.

Thus, the method 100 may improve imaging in certain illumination settings since it may compensate for illumination variations which may otherwise cause an application using the image to make an incorrect decision. Accordingly, the image provided by method 100 may be used to improve decision making in any application likely to be affected by undefined and/or potentially varying illumination such as found in certain illumination settings. Examples of such applications are described in more detail below.

Further, as mentioned previously, the illumination information may be indicative of an orientation of the body surface. In certain applications, the orientation of the body surface may move over time such that as the body surface moves, the illumination of the body surface also changes.

The method 100 may accommodate body surface movement such that the illumination compensation information may be updated as the body surface moves. Thus, in some examples, imaging data may be acquired repeatedly (the frequency of which may depend on the speed of this movement). If the imaging data indicates that the body surface has moved, the illumination information may vary such that the illumination compensation information is to be updated accordingly. On the other hand, if there has been no substantial movement of the body surface, the illumination information may not be significantly changed. In this case, the illumination compensation information may not need to be updated.

Thus, at least one block of the method 100 may be implemented on a repeated basis such that any changes in the orientation and/or illumination may be detected and the illumination compensation information updated accordingly. This capability to accommodate body surface movement may be useful in scenarios where the body surface may move relative to the reference axis while imaging data is acquired. Accordingly, the method 100 may facilitate tracking in time of the body surface while also compensating for any illumination variations. Further examples where this capability might be used is provided in more detail below.

As noted above, a three-dimensional representation for the body surface may be obtained. This three-dimensional representation may be used to assist in determining the illumination information for the body surface.

Contours and other features of the body surface may be illuminated in a certain way depending on the illumination setting. For example, one side of the contour or feature may illuminated with a greater intensity than another side of the contour or feature. This distribution of illumination may be apparent from imaging data (which may define a two-dimensional illumination map), which may be used to determine the illumination information.

Information from the three-dimensional representation may be combined with this imaging data to determine the illumination information (e.g., to define a three-dimensional illumination map, for example). For example, information regarding a contour or feature may be leveraged to help determine a relative positioning between the body surface and a source of the illumination.

Accordingly, the three-dimensional representation may be used to improve the reliability and/or accuracy of determining the illumination information. In other words, additional information regarding the illumination setting may be determined by leveraging the knowledge provided by the three-dimensional representation, which may not otherwise be apparent from the two-dimensional illumination map alone.

Figure 2:
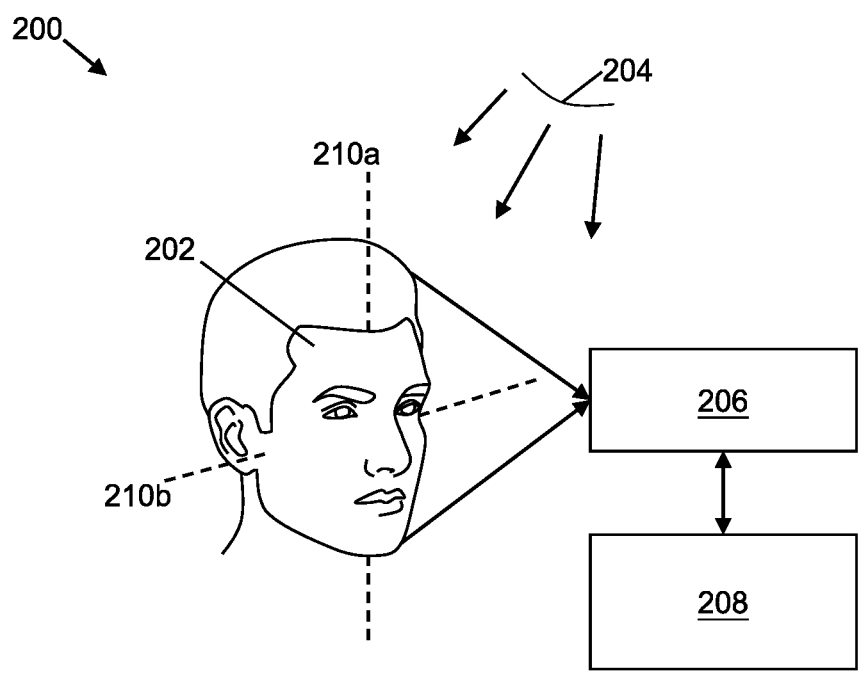
FIG. 2 is a schematic drawing of a system for improving imaging in certain illumination settings according to an embodiment.

FIG. 2 is a schematic drawing of a system 200 for implementing certain methods described herein. For example, the system 200 may implement the method 100 described above. Accordingly, reference is made to the method 100 in the following description of the system 200.

The system 200 of this embodiment is configured to acquire images of a subject's face 202, which is an example of a body surface. According to this embodiment, the body surface referred to in the method 100 comprises a face of a subject and the three-dimensional representation comprises a three-dimensional reconstruction of the face 202.

An illumination source 204 (e.g., a lightbulb, light emitting diode (LED), a natural light source such as sunlight and/or any other source of illumination) provides illumination for the face 202.

The relative positioning of the illumination source 204 and the face 202 affects the distribution of illumination on the face 202. For example, the illumination source 204 is depicted as being above the face 202. Thus, the forehead is closer to the illumination source 204 than the chin, which may lead to the forehead appearing to be illuminated with a greater intensity than the chin. Similarly, certain parts of the face 202 may appear to be illuminated with a greater intensity due to the contours or features of the face 202. For example, the top and front of the nose of the face 202 are facing the illumination source 204 whereas the bottom of the nose is facing away from the illumination source 204. This may mean that the top and front of the nose may be illuminated with a greater intensity than the bottom of the nose.

Accordingly, the distribution of illumination on the face 202 may be uneven due to various factors. In some examples, the relationship between the face 202 and the illumination source 204 may affect the distribution of illumination on the face 202. The relationship may refer to, for example, the distance and/or the positioning of the face 202 (which may also refer to the orientation of the face 202) relative to the illumination source 204.

As referred to previously, movement of the face 202 may affect the distribution of illumination on the face 202. In some examples, a property of the illumination source 204 may additionally or instead affect the distribution of illumination on the face 202. The property of the illumination source 204 may refer to, for example, the spatial illumination profile (e.g., the divergence and/or uniformity) provided by the illumination source, its luminance, spectral content and/or any other property of the illumination source which may affect the distribution of illumination on the face 202.

The system 200 comprises an imaging device 206 (e.g., a camera) for acquiring an image (e.g., 'imaging data') of the face 202 and a processing apparatus 208 for processing the image. The imaging device 206 and the processing apparatus 208 are communicatively coupled to each other for the transfer of imaging data and/or image acquisition instructions therebetween. The imaging device 206 and the processing apparatus 208 may be provided as part of the same device (e.g., such as a smart device such as a phone, tablet, mirror or other device with image acquisition and processing capabilities) or may be provided separately (e.g., the imaging device 206 could be communicatively coupled to a separate processing entity such as a server over a communication network). The processing apparatus 208 may implement certain methods described herein. In this regard, the functionality of the processing apparatus 208 will now be described in relation to the method 100.

The processing apparatus 208 is configured to obtain a three-dimensional representation of the face 202. The three-dimensional representation may be obtained or determined from imaging data of the face 202 (e.g., obtained via one or more images acquired by the imaging device 206 and/or from data provided in a memory accessible to the processing apparatus 208).

The imaging data may be processed to determine the three-dimensional representation. For example, the three-dimensional representation may be based on a model for reconstructing three-dimensional features apparent from two-dimensional imaging data. More than one image may be used to reconstruct the three-dimensional features. For example, images taken at different angles relative to the face 202 may collectively provide information for allowing reconstruction of the three-dimensional contours and features of the face 202.

The processing apparatus 208 is further configured to obtain illumination information for the three-dimensional representation that is indicative of an orientation of the face 202 relative to a reference axis. In this embodiment, the orientation of the face 202 is defined by first and second orthogonal reference axes 210a, 210b. Rotation about the first reference axis 210a may correspond to movement of the face 202 as the subject rotates their head left and right. Rotation about the second reference axis 210b may correspond to movement of the face 202 as the subject lifts/lowers their head up and down.

Illumination information for the three-dimensional representation may be obtained from imaging data of the face 202 (e.g., obtained via one or more images acquired by the imaging device 206 and/or from data provided in a memory accessible to the processing apparatus 208).

The imaging data may comprise an indication of an illumination parameter observed by the imaging device 206 at a particular spatial location on the face 204. The illumination parameter may refer to, for example, an intensity value and/or a spectral content (e.g., red, green and blue intensity level) observed at the particular location by the imaging device 206. The illumination parameter, as observed by the imaging device 206, may depend on certain factors such as: a luminance and/or spectral content of the illumination source 204, the distance between the illumination source 204 and the particular spatial location on the face 202, reflectance of and/or scattering at the particular spatial location, among other factors.

The indication of the illumination parameter may be provided by a pixel intensity value within the imaging data that corresponds to the particular spatial location on the face 204. For example, the face 202 may be illuminated such that a spatial location on the face 202 is observed to have a higher intensity than other spatial locations on the surface. As mentioned previously, the intensity could be higher at the forehead and/or top or front of the nose, as compared to the chin and/or bottom of the nose for the particular illumination setting depicted by FIG. 2. The pixels within the imaging data corresponding to spatial locations such as the forehead and/or top or front of the nose may have intensity values that are higher than other pixels corresponding to other spatial locations such as the chin and/or bottom of the nose. Accordingly, information derived from the imaging data may be used to determine or estimate the illumination parameter for a spatial location on the face 202.

The illumination parameter may have a time dependency such that the illumination parameter may vary as a function of time (e.g., due to a change in illumination level and/or due to movement of the face 202 relative to the illumination source 204). A sequence of images of the face 202 may be used to identify such a variation in the illumination parameter by comparing the sequence of images.

The processing apparatus 208 is configured to determine illumination compensation information to compensate for an illumination variation apparent from the illumination information.

Based on the illumination setting depicted by FIG. 2, the illumination compensation information may take into account the distribution of illumination at the different spatial locations on the face 202 such that, when obtaining an image of the face 202, an illumination compensation factor is applied to the illumination parameter that results in any uneven distribution of illumination apparent in the image being normalized. In other words, the illumination compensation information is configured to normalize an illumination variation in the image.

In an embodiment, determining the illumination compensation information comprises determining a normalization map representing a plurality of spatial locations of the body surface (e.g., the face 202). Each spatial location may be associated with an illumination compensation factor to apply to a corresponding spatial location of the image to correct for the illumination variation in the image.

The processing apparatus 208 is configured to use the illumination compensation information to compensate for the illumination variation in an image of the face 202.

Accordingly, the processing apparatus 208 may use information (such as from imaging data and/or from any other information stored in a database) which can be analyzed to determine whether or not there is any illumination variation for a certain illumination setting. In an image of the face 202, any such illumination variation may be compensated for (e.g., normalized) using the illumination compensation information.

Various applications for methods and apparatus described herein are envisaged. For example, based on the system 200 depicted by FIG. 2, information regarding the face 202 may be determined from an image. Such information may be used for characterization of facial skin, for example. As mentioned previously, a topic of interest in the field of non-obtrusive measurement and monitoring relates to skin sensing for personal care and health applications. Methods and apparatus described herein may enable certain information regarding the facial skin to be determined that takes into account any illumination variation in a certain illumination setting.

Thus, a subject using the system 200 may have a certain level of confidence that an image taken by the imaging device 206 and used for a particular personal care or health application is sufficiently robust and reliable to allow the subject to establish trust in the system 200. Examples of personal care or health applications include: characterization of skin pimples, determining a health status of the skin or of the tissue underlying the skin surface, characterizing blood perfusion, among other examples. Any algorithm that is configured to identify the health status of the skin or tissue underlying the skin surface may base its decision based on certain erroneous assumptions regarding the illumination distribution. For example, an erroneous assumption regarding the illumination distribution may lead to an incorrect classification or identification of a health status of the skin or tissue underlying the skin. One example may be in characterizing skin pimples. Incorrect identification of the type of skin pimple (e.g., caused by an erroneous assumption regarding the illumination distribution) may lead to an incorrect treatment regime being recommended for the type of skin pimple.

Thus, embodiments described herein may facilitate non-obtrusive measurements of the skin, in order to determine a course of action as part of the personal care or health application. A home user may find embodiments described herein to be more reliable and/or robust for imaging where the imaging data is used for making certain decisions for certain applications (e.g., related to a particular personal care or health application), as compared to a system that does not take into account the uncontrolled environment at home.

Apparatus and methods described herein may be used in uncontrolled environments while avoiding erroneous measurements that may otherwise lead to unacceptable or untrusted results for the subject. Consequently, a home user may have a certain degree of confidence that any personal care or health treatment regime based on such results are not or less likely to be compromised as a result of any erroneous measurements resulting from the illumination setting.

Further, by taking into consideration the orientation of the face 202 when determining the illumination compensation information, the subject may have a greater degree of confidence that any movement of their face 202 may not adversely affect the results. Similarly, the subject may find the system 200 easier to use since they may not worry about the orientation of their face 202 when acquiring images of their face 202.

Although FIG. 2 depicts a face 202, the system 200 may be capable of compensating for an illumination variation for any type of body surface. Thus, methods and apparatus described herein may have utility in various applications beyond facial skin characterization. For example, the skin of other parts of the body may be characterized e.g., for certain personal care or health treatment regimes.

Further unclaimed applications may extend beyond skin characterization, for example, in ensuring that an image of any particular body surface (including of an inanimate body or object) takes into account the illumination setting and/or the orientation of the body surface such that any subsequent use or processing of the image is not adversely affected by the illumination setting.

Figure 3:
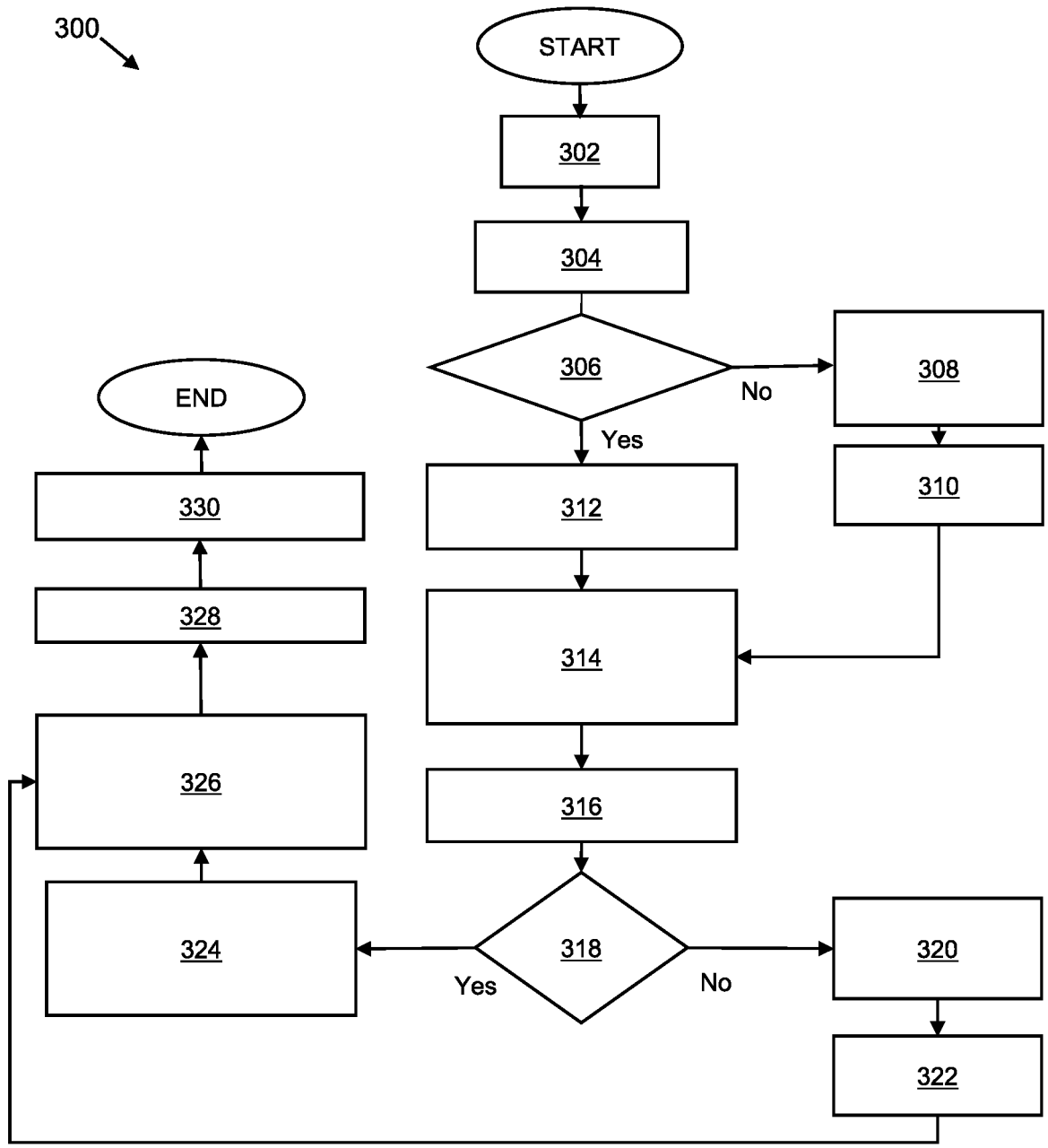
FIG. 3 refers to a method of improving imaging in certain illumination settings according to an embodiment.

FIG. 3 shows a method 300 (e.g., a computer-implemented method) of improving imaging in certain illumination settings. The method 300 may comprise or refer to certain blocks described in relation to FIG. 1. The method 300 may be implemented by certain apparatus or systems described herein such as described in relation to the system 200 of FIG. 2, which is referred to below for ease of reference. Although FIG. 2 refers to a system for characterizing facial skin, the method 300 described below has utility in improving imaging of any body surface or object surface, whether animate or not.

In an embodiment, the method 300 comprises, at block 302, obtaining imaging data for the body surface (e.g., by causing an imaging device 204 to capture an image of the body surface). This imaging data may be used to obtain or determine the three-dimensional representation of the body surface. Accordingly, the method 300 further comprises determining the three-dimensional representation based on the obtained imaging data. The method 300 comprises determining the orientation of the body surface based on an analysis of a three-dimensional reconstruction of the body surface derived from the imaging data for the body surface. The determination of the three-dimensional representation may be performed as described below.

In an embodiment, determining the three-dimensional representation from the imaging data comprises, at block 304 determining whether or not the body surface can be recognized. For example, the method 300 involves checking 306 a memory storing a database of any previously identified body surfaces.

If the body surface is not recognized (i.e., 'no' to block 306), the method 300 comprises determining, at block 308, the three-dimensional representation from the imaging data. This three-dimensional representation may be referred to as a three-dimensional (3D) map or 3D profile, $A_n$, where 'n' refers to the $n^{th}$ image, or most recent image, obtained by block 302. In the example where the body surface is a face, the three-dimensional representation may be referred to as a 3D face map or 3D facial profile.

The method 300 further comprises causing, at block 310, the three-dimensional representation (i.e., $A_n$) associated with the body surface to be stored in a memory (which may be a local memory on a smart device and/or other user apparatus, or in a server or online/cloud storage communicatively coupled to the smart device, user apparatus and/or imaging device 204).

If the body surface is recognized (i.e., 'yes' to block 306), the method 300 comprises obtaining, at block 312, the three-dimensional representation associated with the recognized body surface from the memory (e.g., the same memory used to store the three-dimensional representation obtained via blocks 308 and 310). Since this three-dimensional representation was obtained previously, the 3D map or 3D profile, $A_{n-1}$, obtained from the memory is associated with a previously-obtained image, or the 'n-$1^{th}$' image.

Determining the three-dimensional representation according to blocks 308 and 310 uses computational resource such as processing power and time. By using body surface recognition and retrieving the previously-determined 3D map or 3D profile, $A_{n-1}$, from the memory, less computational resource (e.g., processing power and/or time) may be used when implementing the method 300. From a user's perspective, they may find that characterization of the body surface is quicker if the three-dimensional representation of that body surface has already been determined previously (and retrieved from the memory).

The three-dimensional representation obtained via either blocks 308 and 310 or 312 are then used in other blocks of the method 300, which will be described in more detail below.

Once the three-dimensional representation has been determined for the body surface, the method 300 further comprises, at block 316, obtaining illumination information for the three-dimensional representation. The illumination information may be indicative of the orientation of the body surface relative to a reference axis.

In an embodiment, the imaging device 204 may be caused to acquire, at block 314, at least one other image of the body surface such that up-to-date information regarding the illumination setting and/or the orientation is obtained. If the body surface has moved since the image was obtained at block 302, the other image may provide information indicative of the orientation of the body surface relative to the reference axis.

Thus, the real-time orientation (or at least a time-stamped orientation) of the body surface may be determined based on the imaging data obtained at block 308 (e.g., for tracking purposes). If the body surface has not moved or is unlikely to have moved, it may be possible to use the same image obtained previously (e.g., at block 302) for obtaining the illumination information at block 316. The illumination information may be referred to as an illumination map, $F_n$, where 'n' refers to the $n^{th}$ image obtained at block 314.

The orientation of the body surface may be determined based on information determined from imaging data obtained at one or both of blocks 302 and 314. For example, an analysis of the imaging data when obtaining the three-dimensional representation may provide information regarding the orientation of the body surface. Additionally or alternatively, an analysis of the imaging data when obtaining the illumination information may provide information regarding the orientation of the body surface. For example, a particular distribution of illumination may be indicative of the orientation of the body surface.

In an embodiment, a sequence of imaging data may be obtained, which may be used to, for example, determine if the orientation of the body surface has changed and/or whether there has been any change in the illumination setting since the previous imaging data was obtained. To determine whether or not there has been a change, the method 300 comprises, at block 318, comparing the illumination information, $F_n$, for the $n^{th}$ (i.e., latest) image with the illumination obtained for the n-$1^{th}$ (i.e., a previous) image.

In an embodiment, determining the illumination information from the imaging data comprises comparing, at block 318, the imaging data with previously-obtained imaging data to determine whether or not the imaging data has been obtained in a previous time frame (in other words, whether or not similar or indistinguishable imaging data has been obtained previously). If the imaging data has not been obtained previously (i.e., 'no' at block 318), the method 300 comprises generating, at block 320, the illumination information, $B_n$, from the imaging data (i.e., for the $n^{th}$ image) and causing, at block 322, the illumination information associated with the imaging data to be stored in a memory (which may be the same or different to the memory described above).

If the imaging data has been obtained previously (i.e., 'yes' to block 318), the method 300 comprises obtaining, at block 324, the illumination information, $B_{n-1}$, (i.e., for the n-1$^{th}$ image obtained previously) associated with the imaging data from the memory.

Determining the illumination information according to blocks 320 and 322 uses computational resource such as processing power and time. By retrieving the previously-determined illumination information, $B_{n-1}$, from the memory (e.g., in accordance with block 324), less computational resource (e.g., processing power and/or time) may be used when implementing the method 300. From a user's perspective, they may find that the determination of the illumination information is quicker if the illumination information has already been determined previously (and retrieved from the memory).

In an embodiment, the illumination information determined at blocks 320 and 322 or 324 comprises a three-dimensional illumination map. The three-dimensional illumination map may be generated by using the imaging data obtained at block 314 to map an illumination parameter for a spatial location on the body surface with the corresponding spatial location on the three-dimensional representation. Thus, the three-dimensional illumination map may comprise information regarding contours and/or features of the body surface as well as the corresponding illumination information for those contours and/or features.

In an embodiment, the three-dimensional illumination map represents a plurality of spatial locations of the body surface. Each spatial location of the illumination map may be associated with an illumination parameter indicative of at least one of: a property of an illumination source; and a relative position of the illumination source with respect to the spatial location.

In some embodiments, the illumination parameter for the spatial location of the body surface may be based on an analysis of the obtained imaging data. The analysis may take into account the orientation of the body surface.

In some embodiments, the property of the illumination source may comprise at least one of: a luminance of the illumination source; and a divergence of the illumination source. In some embodiments, the property of the illumination source may refer to the luminance, spatial illumination profile, divergence, spectral content and/or any other properties which may affect the distribution of illumination provided by the illumination source.

Based on the illumination parameter for a particular spatial location of the illumination map as well as knowledge of the property of the illumination source, it may be possible to determine the relative position of the illumination source with respect to the spatial location. In other words, an analysis of the illumination map may be used to estimate the relationship between the body surface and the illumination source. For example, the method 300 may involve estimating certain properties of the illumination source and/or the relationship between the body surface and the illumination source. This estimation may refer to estimating, for example, the direction, luminance, divergence, etc., of the illumination source by numerical calculations using the imaging data (e.g., as obtained at block 314), which may also involve using information regarding the orientation of the body surface to improve or refine the estimate. The numerical calculations may be performed by implementing a ray-tracing method, for example.

The method 300 further comprises determining, at block 326, illumination compensation information (e.g., as referred to in block 104 of the method 100). The illumination compensation information may be referred to as a normalization map, $N_n$, for the $n^{th}$ image. In an embodiment, block 326 may be implemented by identifying any illumination variations apparent from the illumination information, $B_n$ or $B_{n-1}$, to determine the illumination compensation information.

As referred to in block 106 of the method 100, the method 300 further comprises using the illumination compensation information to compensate for the illumination variation in the image of the body surface.

In this embodiment, the method 300 comprises obtaining, at block 328, the image of the body surface.

The method 300 further comprises, at block 330, compensating for the illumination variation in the image (e.g., as obtained at block 328) using the illumination compensation information. For example, the normalization map, $N_n$, may provide a mapping between the illumination compensation factor for a particular spatial location in the map $N_n$ and a corresponding spatial location of the body surface, as apparent from the image. The illumination compensation factor may then be applied to the illumination parameter for the corresponding spatial location to compensate for any illumination variation apparent from the image. Any illumination variations in the image may be normalized such that the image can be used or processed for a particular application while addressing any concerns arising from the illumination setting and/or orientation of the body surface that may otherwise affect the use or processing of the image for the particular application.

Embodiments described herein may implement recognition of a particular subject's (e.g., user's) face (or of any other body surface or object surface) and/or recognition of a certain illumination setting. This recognition may avoid or reduce the need to repeat unnecessary measurements, for example when the same subject is using the system 200 and/or when the ambient light sources are unchanged between sessions. Certain test procedures may be implemented to avoid repeating certain measurements. For example, by performing face (or body surface) recognition, the three-dimensional representation of the subject (or body/object) can be saved in a database and subsequent sessions may retrieve the saved three-dimensional representation. Further, by obtaining imaging data (e.g., capturing a single face front image), any changes in terms of the ambient lighting can be estimated, and in the case that there is not significant change, retrieval of the illumination information from the database may be executed (which may save time and/or processing resources). There may be scenarios where the same subject and same ambient lighting are detected, in which case, the illumination compensation information (e.g., the normalization map) can be retrieved without the need to implement certain blocks of the method 100 (e.g., certain time/processing power-intensive 3D mapping/illumination information determination blocks may not need to be implemented).

As referred to previously, embodiments described herein may enable certain properties of the illumination source to be determined. Certain information may be acquired in order to facilitate this determination. For example, certain methods described herein may involve calibration of the system 200 (e.g., to facilitate more accurate and/or reliable characterization of the body surface). In an example, a calibration object may be imaged in accordance with certain blocks of the methods 100, 300. The imaging device 206 may have a certain sensitivity, imaging property and/or other characteristic which may be affected by the hardware and/or software used to acquire and process the imaging data. For example, the imaging property of the imaging device 206 may be unknown to the processing apparatus 208. By using a calibration object such as a sphere or other shape of a known size, the system 200 may be able to make an improved determination of the three-dimensional representation (e.g., such that the three-dimensional representation has the correct size). In another example, spectral content from the illumination source 204 may be determined by using a calibration object with a known surface characteristic such as spectral reflectance. By measuring the spectral intensity content of the reflected illumination, the system 200 may be able to determine the spectral content of the illumination source, which may improve the determination of the illumination information.

Figure 4:
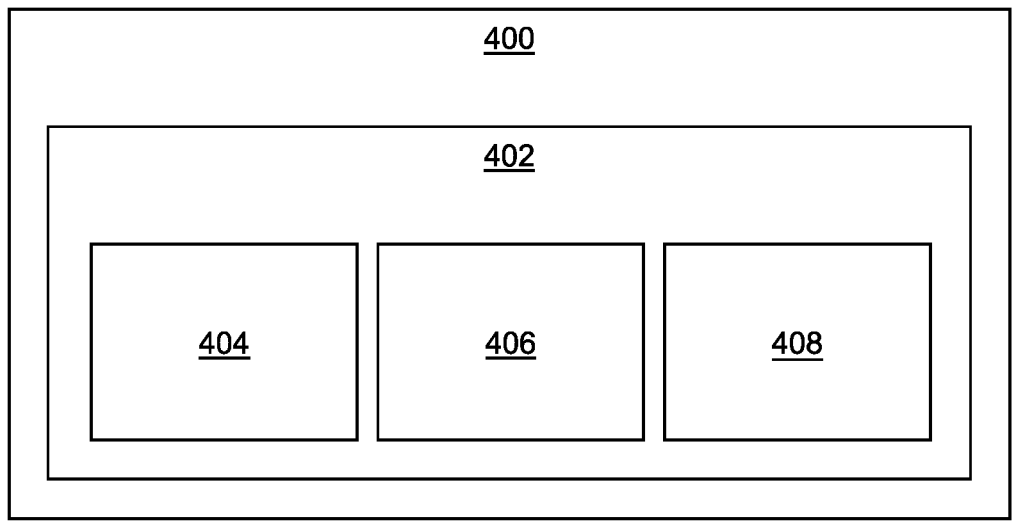
FIG. 4 is a schematic drawing of an apparatus for improving imaging in certain illumination settings according to an embodiment.

FIG. 4 shows an apparatus 400, which may be used for implementing certain methods described herein such as the method 100 and/or the method 300. The apparatus 400 may comprise modules with functionality corresponding to the features described in relation to the system 200 of FIG. 2 such as the processing apparatus 208 thereof.

The apparatus 400 comprises processing circuitry 402 (e.g., which may be provided by the processing apparatus 208 of FIG. 2). The processing circuitry 402 comprises an obtaining module 404 configured to obtain a three-dimensional representation of a body surface. The obtaining module 404 is further configured to obtain illumination information for the three-dimensional representation. The illumination information may be indicative of an orientation of the body surface relative to a reference axis. The processing circuitry 402 further comprises a determining module 406 configured to determine illumination compensation information to compensate for an illumination variation apparent from the illumination information. The processing circuitry 402 further comprises a correcting module (408) configured to use the illumination compensation information to compensate for the illumination variation in an image of the body surface.

Figure 5:
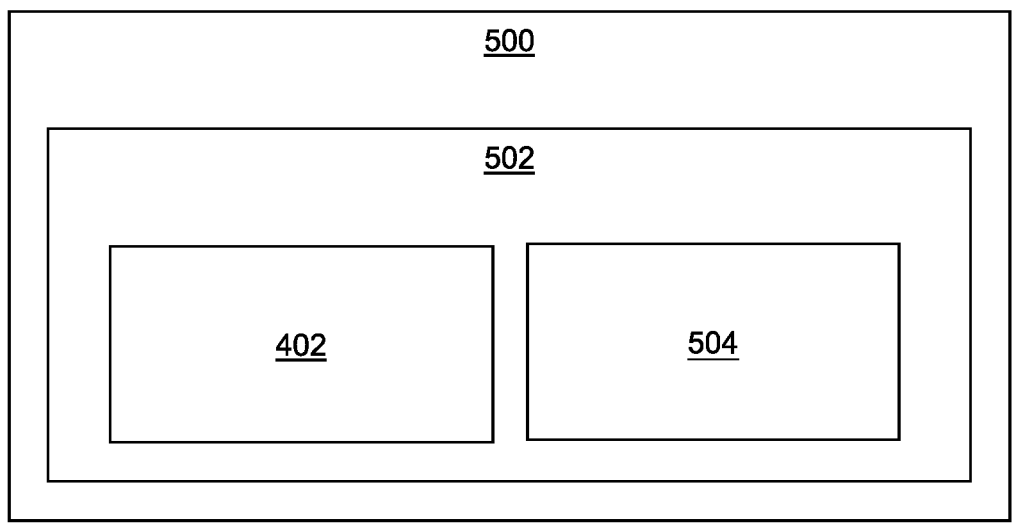
FIG. 5 is a schematic drawing of an apparatus for improving imaging in certain illumination settings according to an embodiment.

FIG. 5 shows an apparatus 500, which may be used for implementing certain methods described herein such as the method 100 and/or the method 300. The apparatus 500 may comprise modules with functionality corresponding to the features described in relation to the system 200 of FIG. 2 such as the processing apparatus 208 thereof and/or the apparatus 400 of FIG. 4.

The apparatus 500 comprises processing circuitry 502 comprising the processing circuitry 402 of FIG. 4. The apparatus 500 further comprises an imaging module 504 configured to cause an imaging device (e.g., the imaging device 206 of FIG. 2) to acquire the image (or indeed any of the imaging data referred to previously) of the body surface. For example, the imaging module 504 may provide an instruction to cause the imaging device 206 to acquire the image or imaging data, for use in certain blocks of methods described herein and/or functional modules of apparatus described herein.

Figure 6:
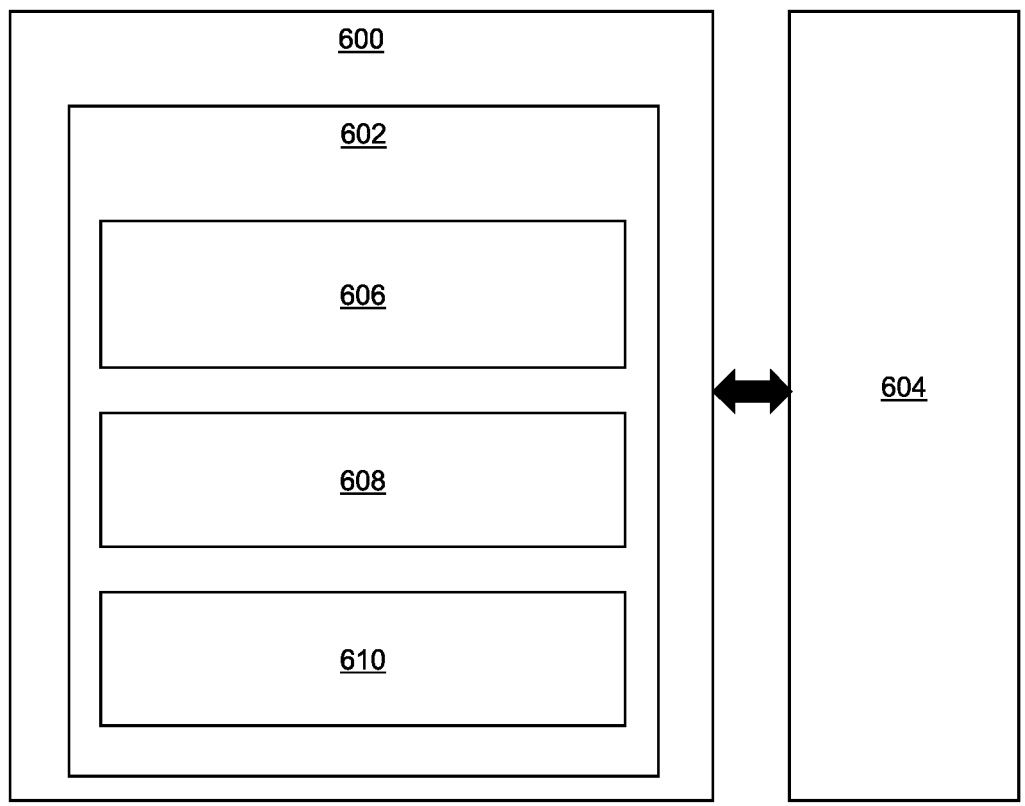
FIG. 6 is a schematic drawing of a machine-readable medium for improving imaging in certain illumination settings according to an embodiment.

FIG. 6 shows a tangible machine-readable medium 600 storing instructions 602 which, when executed by at least one processor 604, cause the at least one processor 604 to implement certain methods described herein (such as the method 100 and/or the method 300). The instructions 602 comprise instructions 606 to obtain a three-dimensional representation of a body surface. The instructions 606 further obtain illumination information for the three-dimensional representation. The illumination information may be indicative of an orientation of the body surface relative to a reference axis. The instructions 602 further comprise instructions 608 to determine illumination compensation information to compensate for an illumination variation apparent from the illumination information. The instructions 602 further comprise instructions 610 to use the illumination compensation information to compensate for the illumination variation in an image of the body surface.

As referred to previously, embodiments may have utility beyond facial skin characterization. For example, embodiments may have utility in characterizing skin of any part of the body.

While the invention has been illustrated and described in detail in the drawings and foregoing description, such illustration and description are to be considered illustrative or exemplary and not restrictive; the invention is not limited to the disclosed embodiments.

One or more features described in one embodiment may be combined with or replace features described in another embodiment. For example, the methods 100 and 300 of FIGS. 1 and 3 may be modified based on features described in relation to the system 200, apparatus 400, 500 of FIGS. 2, 4 and 5, and vice versa.

Embodiments in the present disclosure can be provided as methods, systems or as a combination of machine readable instructions and processing circuitry. Such machine readable instructions may be included on a non-transitory machine (for example, computer) readable storage medium (including but not limited to disc storage, CD-ROM, optical storage, etc.) having computer readable program codes therein or thereon.

The present disclosure is described with reference to flow charts and block diagrams of the method, devices and systems according to embodiments of the present disclosure. Although the flow charts described above show a specific order of execution, the order of execution may differ from that which is depicted. Blocks described in relation to one flow chart may be combined with those of another flow chart. It shall be understood that each block in the flow charts and/or block diagrams, as well as combinations of the blocks in the flow charts and/or block diagrams can be realized by machine readable instructions.

The machine readable instructions may, for example, be executed by a general purpose computer, a special purpose computer, an embedded processor or processors of other programmable data processing devices to realize the functions described in the description and diagrams. In particular, a processor or processing circuitry, or a module thereof, may execute the machine readable instructions. Thus functional modules of the apparatus 400, 500 (for example, the obtaining module 404, determining module 406, correcting module 408 and/or imaging module 504) and other devices described herein may be implemented by a processor executing machine readable instructions stored in a memory, or a processor operating in accordance with instructions embedded in logic circuitry. The term 'processor' is to be interpreted broadly to include a CPU, processing unit, ASIC, logic unit, or programmable gate array etc. The methods and functional modules may all be performed by a single processor or divided amongst several processors.

Such machine readable instructions may also be stored in a computer readable storage that can guide the computer or other programmable data processing devices to operate in a specific mode.

Such machine readable instructions may also be loaded onto a computer or other programmable data processing devices, so that the computer or other programmable data processing devices perform a series of operations to produce computer-implemented processing, thus the instructions executed on the computer or other programmable devices realize functions specified by block(s) in the flow charts and/or in the block diagrams. Further, the teachings herein may be implemented in the form of a computer program product, the computer program product being stored in a storage medium and comprising a plurality of instructions for making a computer device implement the methods recited in the embodiments of the present disclosure.

Elements or steps described in relation to one embodiment may be combined with or replaced by elements or steps described in relation to another embodiment. Other variations to the disclosed embodiments can be understood and effected by those skilled in the art in practising the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computer-implemented method for compensating for illumination variation in an image of a body surface for use in an imaging-based skin sensing system, the method comprising:
obtaining:
a three-dimensional representation of the body surface, and
illumination information for the three-dimensional representation that is indicative of an orientation of the body surface relative to a reference axis;
determining illumination compensation information configured to normalize an illumination variation apparent from the illumination information, wherein determining the illumination compensation information comprises determining a normalization map representing a plurality of spatial locations of the body surface, wherein each spatial location is associated with an illumination compensation factor to apply to a corresponding spatial location of the image to correct for the illumination variation in the image;
determining the orientation of the body surface based on an analysis of a three-dimensional reconstruction of the body surface derived from imaging data for the body surface; and
using the illumination compensation information to compensate for the illumination variation in the image of the body surface to provide a compensated image for use in the imaging-based skin sensing system,
wherein the illumination variation is compensated by distributing illumination evenly across each spatial location on the body surface.

2. The method of claim 1, wherein the compensated image comprises information for use by the imaging-based skin sensing system for characterizing skin on the body surface.

3. The method of claim 2, wherein the illumination information comprises a three-dimensional illumination map representing a plurality of spatial locations of the body surface, wherein each spatial location of the illumination map is associated with an illumination parameter indicative of at least one of: a property of an illumination source; and a relative position of the illumination source with respect to the spatial location.

4. The method of claim 3, wherein determining the illumination information is accomplished by:
obtaining the imaging data for the body surface, and
estimating the illumination parameter for the spatial location of the body surface based on an analysis of the obtained imaging data that takes into account the orientation of the body surface.

5. The method of claim 3, wherein the property of the illumination source comprises:
a luminance of the illumination source, and/or
a divergence of the illumination source.

6. The method of claim 2, wherein determining the illumination compensation information comprises:
obtaining imaging data for the body surface,
determining the illumination information based on the obtained imaging data, and
identifying any illumination variations apparent from the illumination information to determine the illumination compensation information.

7. The method of claim 6, wherein determining the illumination information from the imaging data comprises:
comparing the imaging data with previously-obtained imaging data to determine whether the imaging data has been obtained in a previous time frame,
wherein if the imaging data has not been obtained previously, the method comprises generating the illumination information from the imaging data and causing the illumination information associated with the imaging data to be stored in a memory, and
wherein if the imaging data has been obtained previously, the method comprises obtaining the illumination information associated with the imaging data from the memory.

8. The method of claim 2, wherein obtaining the three-dimensional representation of the body surface comprises:
obtaining imaging data for the body surface, and
determining the three-dimensional representation based on the obtained imaging data.

9. The method of claim 8, wherein determining the three-dimensional representation from the imaging data comprises:
determining whether the body surface can be recognized by checking a memory storing a database of any previously identified body surfaces,
wherein if the body surface is not recognized, the method comprises determining the three-dimensional representation from the imaging data and causing the three-dimensional representation associated with the body surface to be stored in a memory, and
wherein if the body surface is recognized, the method comprises obtaining the three-dimensional representation associated with the recognized body surface from the memory.

10. The method of claim 2, wherein the body surface comprises a face of a subject and the three-dimensional representation comprises a three-dimensional reconstruction of the face.

11. The method of claim 2, wherein using the illumination compensation information to compensate for the illumination variation in the image of the body surface comprises:
obtaining the image of the body surface, and
compensating for the illumination variation in the image using the illumination compensation information.

12. An apparatus for compensating for illumination variation in an image of a body surface for use in an imaging-based skin sensing system, the apparatus comprising processing circuitry, the processing circuitry comprising:
an obtaining module configured to obtain:
a three-dimensional representation of the body surface, and
illumination information for the three-dimensional representation that is indicative of an orientation of the body surface relative to a reference axis, a determining module configured to:
determine illumination compensation information configured to normalize an illumination variation apparent from the illumination information, wherein the illumination compensation information is determined by determining a normalization map representing a plurality of spatial locations of the body surface, wherein each spatial location is associated with an illumination compensation factor to apply to a corresponding spatial location of the image to correct for the illumination variation in the image,
determine the orientation of the body surface based on an analysis of a three-dimensional reconstruction of the body surface derived from imaging data for the body surface; and
a correcting module configured to use the illumination compensation information to compensate for the illumination variation in the image of the body surface to provide a compensated image for use in the imaging-based skin sensing system, wherein the illumination variation is compensated by distributing illumination evenly across each spatial location on the body surface.

13. The apparatus of claim 12, further comprising an imaging module configured to cause an imaging device to acquire the image of the body surface.

14. A non-transitory, machine-readable medium storing instructions for compensating for illumination variation in an image of a body surface for use in an imaging-based skin sensing system, which, when executed by at least one processor, causes the at least one processor to:
obtain:
a three-dimensional representation of the body surface, and
illumination information for the three-dimensional representation that is indicative of an orientation of the body surface relative to a reference axis;
determine illumination compensation information configured to normalize an illumination variation apparent from the illumination information, wherein the illumination compensation information is determined by determining a normalization map representing a plurality of spatial locations of the body surface, wherein each spatial location is associated with an illumination compensation factor to apply to a corresponding spatial location of the image to correct for the illumination variation in the image;
determine the orientation of the body surface based on an analysis of a three-dimensional reconstruction of the body surface derived from imaging data for the body surface; and
use the illumination compensation information to compensate for the illumination variation in the image of the body surface to provide a compensated image for use in the imaging-based skin sensing system, wherein the illumination variation is compensated by distributing illumination evenly across each spatial location on the body surface.

15. The non-transitory, machine-readable medium of claim 14, wherein the compensated image comprises information for use by the imaging-based skin sensing system for characterizing skin on the body surface.

16. The non-transitory, machine-readable medium of claim 15, wherein the illumination information comprises a three-dimensional illumination map representing a plurality of spatial locations of the body surface, wherein each spatial location of the illumination map is associated with an illumination parameter indicative of at least one of: a property of an illumination source; and a relative position of the illumination source with respect to the spatial location.

17. The non-transitory, machine-readable medium of claim 16, wherein determining the illumination information is accomplished by:
obtaining the imaging data for the body surface, and
estimating the illumination parameter for the spatial location of the body surface based on an analysis of the obtained imaging data that takes into account the orientation of the body surface.

18. The non-transitory, machine-readable medium of claim 16, wherein the property of the illumination source comprises:
a luminance of the illumination source, and/or
a divergence of the illumination source.

19. The non-transitory, machine-readable medium of claim 15, wherein determining the illumination compensation information comprises:
obtaining imaging data for the body surface,
determining the illumination information based on the obtained imaging data, and
identifying any illumination variations apparent from the illumination information to determine the illumination compensation information.

20. The non-transitory, machine-readable medium of claim 19, wherein determining the illumination information from the imaging data comprises:
comparing the imaging data with previously-obtained imaging data to determine whether the imaging data has been obtained in a previous time frame,
wherein if the imaging data has not been obtained previously, the illumination information is generated from the imaging data and the illumination information associated with the imaging data is caused to be stored in a memory, and
wherein if the imaging data has been obtained previously, the illumination information associated with the imaging data is obtained from the memory.

* * * * *